United States Patent [19]

Witiak et al.

[11] Patent Number: 5,356,891
[45] Date of Patent: Oct. 18, 1994

[54] PHENYLALKYL AMINE DERIVATIVES HAVING ANTI-ISCHAEMIC ACTIVITY

[76] Inventors: Donald T. Witiak; Ineke van Wijngaarden; Raghunathan V. Nair; Josephus H. M. Lange; Jacobus A. J. den Hartog, all of C. J. Van Houtenlaan 36, Weesp, Netherlands

[21] Appl. No.: 974,816

[22] Filed: Nov. 16, 1992

Related U.S. Application Data

[63] Continuation of Ser. No. 778,754, Oct. 18, 1991, abandoned, which is a continuation of Ser. No. 586,214, Sep. 21, 1990, abandoned.

[30] Foreign Application Priority Data

Sep. 22, 1989 [EP] European Pat. Off. ........ 89202383.9

[51] Int. Cl.$^5$ ............... A01N 43/46; A01N 43/40; C07D 211/68; C07D 215/04
[52] U.S. Cl. ............... 514/212; 514/228.2; 514/233.8; 514/248; 514/255; 514/314; 514/318; 514/321; 514/414; 540/524; 544/62; 544/111; 544/124; 544/146; 544/148; 544/349; 544/360; 544/377; 546/173; 546/194; 546/197; 548/526
[58] Field of Search ............... 546/197, 173, 194; 544/62, 111, 124, 146, 148, 349, 360, 377; 540/524; 548/526; 514/212, 228.2, 233.8, 248, 255, 314, 318, 321, 414

[56] References Cited

U.S. PATENT DOCUMENTS

| | | | |
|---|---|---|---|
| 4,535,159 | 8/1985 | Forné et al. | 546/197 |
| 4,536,500 | 8/1985 | Bourgery et al. | 546/197 |
| 4,942,169 | 7/1990 | Sugimoto et al. | 546/197 |
| 5,256,673 | 10/1993 | Böttcher et al. | 514/338 |

FOREIGN PATENT DOCUMENTS 4916873  4/1974  Japan .................. 546/197

*Primary Examiner*—C. Warren Ivy
*Assistant Examiner*—Raymond Covington
*Attorney, Agent, or Firm*—Stevens, Davis, Miller & Mosher

[57] ABSTRACT

The present invention relates to compounds having anti-ischaemic activity of the formula

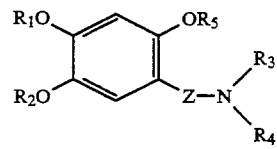

wherein $R_1$, $R_2$, $R_3$, $R_4$, $R_5$ and Z are as defined herein. The present invention further relates to a method of preparing such compounds, as well as compositions having anti-ischaemic activity which comprise such compounds and a method of treating ischaemia.

3 Claims, No Drawings

PHENYLALKYL AMINE DERIVATIVES HAVING ANTI-ISCHAEMIC ACTIVITY

This application is a continuation of application Ser. No. 07/778,754, filed Oct. 18, 1991, now abandoned which in turn is a continuation of application Ser. No. 07/586,214, filed Sep. 21, 1990, now abandoned.

The invention relates to a group of new phenylalkyl amine derivatives having interesting anti-ischaemic activity, to a method of preparing said compounds, and to pharmaceutical compositions comprising at least one of these compounds as the active component.

There is an increasing clinical interest in an effective pharmalogical symptomatic treatment for cerebral and peripheral ischaemic diseases. In patients suffering from these diseases the impaired blood supply causes an inadequate delivery of oxygen and other nutrients to the tissue as well as a diminished removal of metabolic waste products resulting in structural injury and functional deterioration.

The object of the present invention is to provide active compounds with anti-ischaemic properties.

It has been found surprisingly that compounds of formula 1

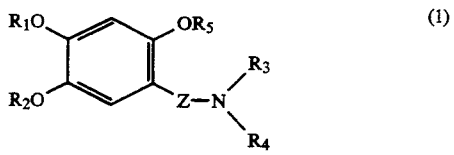

wherein $R_1 + R_2$ together form an alkylene group having 1-3 C-atoms which may be substituted with one or more alkyl group(s) having 1-3 C-atoms;

Z is methylene optionally substituted with one or two alkyl group(s) having 1-3 C-atoms, or with one phenyl group or phenylalkyl group with 1-3 C-atoms in the alkyl group, which phenyl groups may be substituted with a group $(R_6)_p$ wherein $R_6$ is halogen, hydroxy, alkyl or hydroxyalkyl having 1-5 C-atoms, alkoxy having 1-3 C-atoms, S-alkyl, S(O)-alkyl or $S(O)_2$-alkyl having 1-3 C-atoms, amino, mono- or dialkylamino having 1-3 C-atoms per alkyl group, trifluoromethyl, trifluoromethoxy, a sulphonylamido group $SO_2NHR$ or a carbalkoxy group COOR wherein R is alkyl having 1-4 C-atoms, the group COOH, $SO_3H$, $COHN_2$, the amidino group or cyano group, and p has the value 0-3;

$R_3$ and $R_4$ independent of each other represent hydrogen, alkyl having 1-10 C-atoms, alkenyl or alkynyl having 3-10 C-atoms, cycloalkyl having 3-8 C-atoms, cycloalkylalkyl having 3-8 ring atoms and 1-5 C-atoms in the alkyl group, phenylalkyl or heteroaryl-alkyl having 1-5 C-atoms in the alkyl group, phenylalkenyl, heteroarylalkenyl, phenylalkynyl or heteroaryl-alkynyl group having 3-5 C-atoms in the alkenyl group or alkynyl group, which groups $R_3$ and $R_4$ may be substituted with a group $(R_6)_p$ wherein $R_6$ and p have the above mentioned meanings, or wherein $R_3 + R_4$ together with the nitrogen atom form a saturated or unsaturated heterocyclic group of 5-7 ring atoms, which may contain a second hetero-atom from the group consisting of oxygen, sulphur and nitrogen, which ring may be substituted with a group $(R_6)_p$ wherein $R_6$ and p have the above mentioned meanings, or with phenylalkyl, phenylalkenyl, thienylalkenyl, pyridinylalkenyl, phenylalkynyl, thienylalkynyl or pyridinylalkynyl having at most 3 C-atoms in the alkyl, alkenyl or alkynyl part, which groups may be substituted with a group $(R_6)_p$ wherein $R_6$ and p have the above-mentioned meanings, or which ring may be annelated with a phenyl group;

$R_5$ is alkyl having 1-12 C-atoms, alkenyl or alkynyl having 3-12 C-atoms, cycloalkyl having 3-8 C-atoms, cycloalkyl-alkyl having 3-8 ring atoms and 1-5 C-atoms in the alkyl group, phenylalkyl or heteroaryl-alkyl having 1-5 C-atoms in the alkyl sub-group, phenylalkenyl, heteroaryl-alkenyl, phenylalkynyl or heteroaryl-alkynyl having 3-5 C-atoms in the alkenyl sub-group or alkynyl sub-group, which groups may be substituted with a group $(R_6)_p$, wherein $R_6$ and p have the above-mentioned meanings, and which alkyl sub-groups, alkenyl sub-groups and alkynyl sub-groups may contain a group —O—, —S— or CO, prodrugs and pharmaceutically acceptable acid addition salts thereof have interesting and valuable anti-ischaemic properties.

Prodrugs are derivatives of these compounds which as such are inactive, from which, after splitting off an easily removable group, for example an ester group or an ether group, an active compound of formula 1 is obtained. Suitable acids with which suitable addition salts can be formed are, for example, hydrochloric acid, sulphuric acid, phosphoric acid, nitric acid, and organic acids like citric acid, fumaric acid, maleic acid, tartaric acid, acetic acid, benzoic acid, p-toluene sulphonic acid, methane sulphonic acid, etc.

One or more centres of chirality may be present in the compounds having formula 1. The invention relates both to racemates and the individual isomers of the compounds having formula 1.

The anti-ischaemic activity of the compounds has been determined by means of the in vivo hypobaric hypoxia test and the in vitro cardiomyocytes test. These tests were used to characterize substances with cerebro- and/or peripheral-protective activity.

1) Hypobaric activity in vivo

Cerebro-protective activity was determined by measuring the prolongation of the survival time of conscious mice under hypobaric conditions.

Groups of 3 overnight fasted male NMRI mice (15–20 g) are dosed ip (30 mg/kg), 30 minutes before being placed in a chamber at hypobaric pressure of 200 mBar. The prolongation of the survival time is expressed in percentage increase in respiration time, compared to that of the placebo treated control group.

2) Cardiomyocytes in vitro:

Cyto-protective properties were determined in an in vitro model using isolated calcium tolerant cardiomyocytes according to L. Verdonk et al (Life Sciences, vol.38, (1986) 765–772).

Cardiomyocytes were isolated from male Wistar rat hearts. Rod shaped cells were incubated with the compound to be tested for 30 min. Injury was induced by e.g. veratrine (100/ug/ml) or by hypoxia upon which the cells became rounded unless protected by the compound. After 20 min. the remaining rod-shaped cells were counted and the protecting efficacy of the compound was determined.

The compounds having formula 1, wherein the symbols have the above-mentioned meaning are new compounds which can be prepared according to methods known per se.

For example compounds having formula 1 can be obtained by first preparing a compound having formula 2

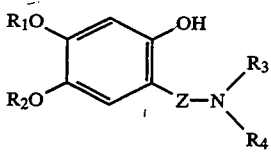

wherein $R_1$-$R_4$ and Z have the above mentioned meanings, by reacting a compound of the formula 3

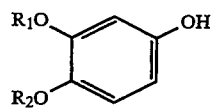

with a compound of the formula $R_3R_4NH$ and an aldehyde of the formula $R_7CHO$, in which formulae $R_1$-$R_4$ have the above mentioned meaning and $R_7$ is hydrogen, alkyl having 1–3 C-atoms, phenyl or phenylalkyl, which phenyl groups may be substituted with a group $(R_6)_p$ wherein $R_6$ and p have the above mentioned meanings. This so-called Mannich-reaction is preferably carried out in an inert organic solvent, such as ethanol or acetonitrile.

The starting compounds of formula 3 are known or can be obtained analogously to known compounds.

The so-obtained compounds of formula 2 can be converted into the corresponding compounds of formula 1 wherein $R_5$ has the above mentioned meanings by means of a reaction with a compound of the formula $R_5$-X, wherein X is a so-called leaving group, for example halogen. This reaction is preferably carried out in an inert solvent such as dimethylsulphoxide (DMSO), N,N-dimethylformamide (DMF) and the like, in the presence of a suitable case such as sodium hydride or potassium tert-butoxide and the like. Sometimes the addition of sodium iodide is desirable. The reaction may be carried out at somewhat elevated temperatures.

Compounds of the formula 1 wherein $R_4$ is hydrogen can be obtained by the reductive amination reaction of a compound of formula 4

$$\underset{R_2O}{\overset{R_1O}{\phantom{X}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \overset{OR_5}{\underset{\underset{O}{\overset{\|}{C-R_7}}}{\phantom{X}}} \quad (4)$$

with an amine of the formula $R_3NH_2$, in which formulae $R_1$-$R_3$ and $R_5$ have the meanings given in formula 1, and $R_7$ has the meaning given above. Addition of an acid catalyst may be desirable to enhance the reaction rate. The reaction is preferably carried out in an inert solvent. Removal of water formed during the reaction is preferably carried out during the amination step by means of azeotropic distillation with an aromatic solvent, for example benzene or toluene. The reductive step of this process can be carried out with a suitable reducing agent such as $LiAlH_4$ in an inert solvent, for example tetrahydrofuran or diethyl ether, or by other known reductive amination methods (see for example Russ. Chem. Rev. 49, 14 (1980), or Synthesis, 135 (1975)).

Starting compounds of the formula 4 are known (J. Chem. Soc. Perkin I, 305, (1974); Synth. Commun. 10, 9, (1980)), or can be prepared in a similar manner.

The so-obtained compounds of formula 1, wherein $R_4$ is hydrogen can be converted into the corresponding compounds wherein $R_4$ has another meaning by reductive alkylation with a suitable aldehyde in the presence of a reducing agent such as sodium cyanoborohydride in an inert solvent.

The above described reductive amination of a compound of formula 4 can also be carried out with a secondary amine of the formula $R_3R_4NH$, leading directly to the desired end products of formula 1.

The invention will be further illustrated by means of the following examples.

EXAMPLE I

5-N,N-diethylaminomethyl-6-hydroxy-1,3-benzodioxole

To a stirred solution of 5-hydroxy-1,3-benzodioxole (5.0 g, 36.2 mmol) and diethylamine (2.9 g, 39.7 mmol) in ethanol (25 ml) was added dropwise 37% aqueous formaldehyde (3.2 g, 39.5 mmol). The reaction mixture was stirred at room temperature for 4 hours and evaporated in vacuo. The remaining oil (7.4 g) was crystallized from methanol; melting point 52°–54° C. (compound no.1).

In a similar manner the compounds of formula 2 wherein Z and $R_1$-$R_4$ have the meaning indicated in table A were prepared:

TABLE A

| No. | $R_1 + R_2$ | $R_3$ | (+) | $R_4$ | Z | m.p. (°C.) |
|---|---|---|---|---|---|---|
| 2 | —(CH$_2$)— | —(CH$_2$)$_2$O(CH$_2$)$_2$— | | | CH$_2$ | 86–88 |
| 3 | —(CH$_2$)— | —(CH$_2$)$_5$— | | | CH$_2$ | 50–51 |
| 4 | —(CH$_2$)— | —(CH$_2$)$_2$N(CH$_3$)(CH$_2$)$_2$— | | | CH$_2$ | 95–97 |
| 5 | —(CH$_2$)— | —(CH$_2$)$_2$N(CH$_2$CH$_2$CH$_3$)(CH$_2$)$_2$— | | | CH$_2$ | oil |
| 6 | —(CH$_2$)$_2$— | C$_2$H$_5$ | | C$_2$H$_5$ | CH$_2$ | oil |
| 7 | —(CH$_2$)$_2$— | —(CH$_2$)$_5$— | | | CH$_2$ | oil |
| 8 | —(CH$_2$)— | —(CH$_2$)$_2$N(CH(C$_6$H$_5$)$_2$)(CH$_2$)$_2$— | | | CH$_2$ | 160–161 |
| 9 | —(CH$_2$)— | —(CH$_2$)$_5$— | | | CH(C$_6$H$_5$) | 180 (dec.), (HBr-salt) |
| 10 | —(CH$_2$)— | H | | C$_2$H$_5$ | CH(C$_6$H$_5$) | oil |

EXAMPLE II

5-N,N-diethylaminomethyl-6-phenylmethoxy-1,3-benzodioxole.HCl

To a mixture of 5-N,N-diethylaminomethyl-6-hydroxy-1,3-benzodioxole (2.0 g, 9 mmol), sodium iodide (0.135 g, 0.9 mmol) and potassium-tert-butoxide (1.19 g, 10.5 mmol) in DMSO (30 ml) was added benzyl bromide (1.54 g, 9 mmol). The stirred mixture was heated at 80° C. for 3 hours. Thereafter, the mixture was allowed to attain room temperature, water was added and the resulting solution was extracted with dichloromethane, washed with a 2N sodium hydroxide solution and brine respectively, dried over $MgSO_4$, filtered and evaporated in vacuo. The obtained brown oil (3.7 g) was purified by flash chromatography (silica gel, dichloromethane/methanol/ammonia(25%)=95/4.5/0.5) to give pure 5-N,N-diethylaminomethyl-6-phenylmethoxy-1,3-benzodioxole (2.0 g, yield 71%). A mixture of isopropanol and diethyl ether was added to the obtained product, and the resulting solution was saturated with gaseous hydrogen chloride. After evaporation of the solvents in vacuo 5-N,N-diethylaminomethyl-6-phenylmethoxy-1,3-benzodioxole.HCl (1.4 g, yield 45%) was obtained as a white solid; m.p. 122°–123° C. (compound no. 11).

In a similar manner the compounds of formula 1 wherein Z and $R_1$–$R_5$ have the meaning indicated in table B were prepared:

TABLE B

| No | R1 + R2 | R3 | (+) R4 | R5 | Z | salt | m.p. (°C.) |
|---|---|---|---|---|---|---|---|
| 12 | —(CH$_2$)— | CH$_3$ | CH$_3$ | n-C$_3$H$_7$ | CH$_2$ | HCl.0.1H$_2$O | 138–140 |
| 13 | —(CH$_2$)— | CH$_3$ | CH$_3$ | n-C$_4$H$_9$ | CH$_2$ | HCl | 140–142 |
| 14 | —(CH$_2$)— | CH$_3$ | CH$_3$ | n-C$_5$H$_{11}$ | CH$_2$ | HCl | 131–133 |
| 15 | —(CH$_2$)— | CH$_3$ | CH$_3$ | n-C$_6$H$_{13}$ | CH$_2$ | citric acid | 119–121 |
| 16 | —(CH$_2$)— | CH$_3$ | CH$_3$ | n-C$_8$H$_{17}$ | CH$_2$ | HCl | 113–115 |
| 17 | —(CH$_2$)— | CH$_3$ | CH$_3$ | n-C$_{12}$H$_{25}$ | CH$_2$ | HCl | 120–122 |
| 18 | —(CH$_2$)— | CH$_3$ | CH$_3$ | (CH$_2$)$_3$C$_6$H$_5$ | CH$_2$ | HCl | 167–169 |
| 19 | —(CH$_2$)— | C$_2$H$_5$ | C$_2$H$_5$ | n-C$_3$H$_7$ | CH$_2$ | HCl.0.1H$_2$O | 111–113 |
| 20 | —(CH$_2$)— | C$_2$H$_5$ | C$_2$H$_5$ | n-C$_4$H$_9$ | CH$_2$ | HCl.0.1H$_2$O | 122–124 |
| 21 | —(CH$_2$)— | C$_2$H$_5$ | C$_2$H$_5$ | n-C$_5$H$_{11}$ | CH$_2$ | HCl | 120–122 |
| 22 | —(CH$_2$)— | C$_2$H$_5$ | C$_2$H$_5$ | n-C$_6$H$_{13}$ | CH$_2$ | HCl | 127–129 |
| 23 | —(CH$_2$)— | C$_2$H$_5$ | C$_2$H$_5$ | n-C$_8$H$_{17}$ | CH$_2$ | HCl | 131–132 |
| 24 | —(CH$_2$)— | C$_2$H$_5$ | C$_2$H$_5$ | n-C$_{12}$H$_{25}$ | CH$_2$ | HCl | 110–112 |
| 25 | —(CH$_2$)— | C$_2$H$_5$ | C$_2$H$_5$ | (CH$_2$)$_3$C$_6$H$_5$ | CH$_2$ | HCl | 115–117 |
| 26 | —(CH$_2$)— | n-C$_3$H$_7$ | n-C$_3$H$_7$ | n-C$_5$H$_{11}$ | CH$_2$ | HCl | 111–113 |
| 27 | —(CH$_2$)— | i-C$_3$H$_7$ | i-C$_3$H$_7$ | n-C$_5$H$_{11}$ | CH$_2$ | HCl | 117–119 |
| 28 | —(CH$_2$)— | n-C$_4$H$_9$ | n-C$_4$H$_9$ | n-C$_5$H$_{11}$ | CH$_2$ | HCl | 114–116 |
| 29 | —(CH$_2$)— | n-C$_5$H$_{11}$ | n-C$_5$H$_{11}$ | n-C$_5$H$_{11}$ | CH$_2$ | oxalic acid | 124–126 |
| 30 | —(CH$_2$)— | n-C$_6$H$_{13}$ | n-C$_6$H$_{13}$ | n-C$_5$H$_{11}$ | CH$_2$ | oxalic acid | 100–102 |
| 31 | —(CH$_2$)— | cyclohexyl | cyclohexyl | n-C$_5$H$_{11}$ | CH$_2$ | HCl | 183–185 |
| 32 | —(CH$_2$)— | C$_2$H$_5$ | C$_2$H$_5$ | CH$_2$C(O)C$_6$H$_5$ | CH$_2$ | fumaric acid | 161–163 |
| 33 | —(CH$_2$)— | —(CH$_2$)$_5$— | | n-C$_4$H$_9$ | CH$_2$ | HCl | 162–164 |
| 34 | —(CH$_2$)— | —(CH$_2$)$_5$— | | n-C$_5$H$_{11}$ | CH$_2$ | HCl | 151–153 |
| 35 | —(CH$_2$)— | —(CH$_2$)$_5$— | | (CH$_2$)$_2$CH(CH$_3$)$_2$ | CH$_2$ | HCl | 192–194 |
| 36 | —(CH$_2$)— | —(CH$_2$)$_5$— | | CH$_2$C$_6$H$_5$ | CH$_2$ | free base | 73–75 |
| 37 | —(CH$_2$)— | —(CH$_2$)$_5$ | | —CH$_2$-2-cyanophenyl | CH$_2$ | free base | 95–96 |
| 38 | —(CH$_2$)— | —(CH$_2$)$_5$— | | CH$_2$-2-Cl—C$_6$H$_4$ | CH$_2$ | free base | 82–84 |
| 39 | —(CH$_2$)— | —(CH$_2$)$_5$— | | CH$_2$-3-Cl—C$_6$H$_4$ | CH$_2$ | HCl | 213–216 |
| 40 | —(CH$_2$)— | —(CH$_2$)$_5$— | | CH$_2$-4-Cl—C$_6$H$_4$ | CH$_2$ | HCl | 207–209 |
| 41 | —(CH$_2$)— | —(CH$_2$)$_5$— | | CH$_2$-2-F—C$_6$H$_4$ | CH$_2$ | free base | 101–103 |
| 42 | —(CH$_2$)— | —(CH$_2$)$_5$— | | CH$_2$-3-F—C$_6$H$_4$ | CH$_2$ | HCl.¼CH$_3$OH | 180–182 |
| 43 | —(CH$_2$)— | —(CH$_2$)$_5$— | | CH$_2$-4-F—C$_6$H$_4$ | CH$_2$ | HCl.¼CH$_3$OH | 211–213 |
| 44 | —(CH$_2$)— | —(CH$_2$)$_5$— | | —(CH$_2$)$_3$—C$_6$H$_5$ | CH$_2$ | HCl | 175–177 |
| 45 | —(CH$_2$)— | (tetrahydronaphthalene-fused bicyclic group) | | n-C$_5$H$_{11}$ | CH$_2$ | HCl | 157–159 |
| 46 | —(CH$_2$)— | —(CH$_2$)$_4$— | | n-C$_5$H$_{11}$ | CH$_2$ | HCl | 156–158 |
| 47 | —(CH$_2$)— | —(CH$_2$)$_2$O(CH$_2$)$_2$— | | n-C$_4$H$_9$ | CH$_2$ | HCl | 212–215 |
| 48 | —(CH$_2$)— | —(CH$_2$)$_2$N(CH$_3$)(CH$_2$)$_2$— | | (CH$_2$)$_3$C$_6$H$_5$ | CH$_2$ | 2HCl | 245 (dec) |
| 49 | —(CH$_2$)— | —(CH$_2$)$_2$N(CH$_3$)(CH$_2$)$_2$— | | n-C$_4$H$_9$ | CH$_2$ | HCl.2H$_2$O | 197–200 |
| 50 | —(CH$_2$)— | —(CH$_2$)$_2$N(CH$_3$)(CH$_2$)$_2$— | | trans-CH$_2$CHCHC$_6$H$_5$ | CH$_2$ | free base | 225–227 |
| 51 | —(CH$_2$)— | —(CH$_2$)$_2$N(CH$_2$CH$_2$CH$_3$)(CH$_2$)$_2$— | | n-C$_5$H$_{11}$ | CH$_2$ | 2HCl | 230 (dec.) |
| 52 | —(CH$_2$)— | —(CH$_2$)$_2$N(CH(C$_6$H$_5$)$_2$)(CH$_2$)$_2$— | | CH$_3$ | CH$_2$ | 2HCl | 222–224 |
| 53 | —(CH$_2$)— | —(CH$_2$)$_2$N(CH(C$_6$H$_5$)$_2$)(CH$_2$)$_2$— | | n-C$_4$H$_9$ | CH$_2$ | 2HCl | 230–231 |
| 54 | —(CH$_2$)— | —(CH$_2$)$_2$N(CH$_2$-3,4-OCH$_2$O—C$_6$H$_3$)(CH$_2$)$_2$— | | n-C$_4$H$_9$ | CH$_2$ | 2HCl | 257–260 |
| 55 | —(CH$_2$)$_2$— | C$_2$H$_5$ | C$_2$H$_5$ | (CH$_2$)$_3$C$_6$H$_5$ | CH$_2$ | fumaric acid | 131–133 |
| 56 | —(CH$_2$)$_2$— | C$_2$H$_5$ | C$_2$H$_5$ | n-C$_5$H$_{11}$ | CH$_2$ | fumaric acid | 107–109 |
| 57 | —(CH$_2$)$_2$— | —(CH$_2$)$_5$— | | (CH$_2$)$_3$C$_6$H$_5$ | CH$_2$ | HCl | 168–170 |
| 58 | —(CH$_2$)$_2$— | —(CH$_2$)$_5$— | | n-C$_5$H$_{11}$ | CH$_2$ | HCl | 169–171 |
| 59 | —(CH$_2$)$_2$— | —(CH$_2$)$_5$— | | CH$_3$ | CH(C$_6$H$_5$) | HBr | 205 (dec.) |
| 60 | —(CH$_2$)— | H | C$_2$H$_5$ | n-C$_3$H$_7$ | CH(C$_6$H$_5$) | HBr | 178–180 |
| 61 | —(CH$_2$)— | C$_2$H$_5$ | C$_2$H$_5$ | n-C$_3$H$_7$ | CH(C$_6$H$_5$) | HBr | 110–112 |

TABLE C

| No | R1 + R2 | R3 | R4 | R5 | salt | m.p. (°C.) |
|---|---|---|---|---|---|---|
| 63 | —(CH$_2$)— | CH$_3$ | CH$_3$ | C(O)-n-C$_3$H$_7$ | HCl | 184–186 |

TABLE C-continued

| No | R1 + R2 | R3 | R4 | R5 | salt | m.p. (°C.) |
|---|---|---|---|---|---|---|
| 64 | —(CH2)— | CH3 | CH3 | C(O)-n-C4H9 | HCl | 154–158 |
| 65 | —(CH2)— | C2H5 | C2H5 | C(O)-n-C4H9 | HCl | 123–125 |

TABLE D

| No | R1 + R2 | R3 | R4 | R5 | salt | m.p. (°C.) |
|---|---|---|---|---|---|---|
| 67 | —(CH2)— | H | C2H5 | n-C7H15 | HCl | 138–140 |
| 68 | —(CH2)— | H | C2H5 | (CH2)3C6H5 | HCl | 127–129 |
| 69 | —(CH2)— | H | (CH2)2C6H5 | n-C4H9 | free base | 157–159 |
| 70 | —(CH2)— | H | CH2C6H5 | n-C5H11 | HCl | 116–118 |
| 71 | —(CH2)— | H | (CH2)2-3,4-(OCH3)2—C6H3 | n-C5H11 | HCl | 143–145 |
| 72 | —(CH2)— | H | (CH2)2-3,4-(OCH3)2—C6H3 | (CH2)3C6H5 | HCl | 117–119 |
| 73 | —(CH2)— | H | (CH2)2-3,4-(OCH3)2—C6H3 | CH2C6H5 | HCl | 185–188 |
| 74 | —(CH2)— | H | (CH2)2-3,4-(OCH3)2—C6H3 | (CH2)5C6H5 | HCl | 138–140 |
| 75 | —(CH2)— | H | (CH2)2-3,4-OCH2O—C6H3 | CH2C6H5 | HCl | 188–190 |

EXAMPLE III 2-(N,N-diethylaminomethyl)-4,5-methylenedioxyphenyl-n-butyrate.HCl A mixture of 5-N,N-diethylaminomethyl-6-hydroxy-1,3-benzodioxole (3.0 g, 13.5 mmol), n-butyric anhydride (2.15 g, 13.6 mmol) and a drop of concentrated sulphuric acid was stirred at room temperature for 15 minutes. Crushed ice was added to the clear solution. The pH of the solution was made alkaline (pH=10–11) by means of a 10% NaOH solution. The mixture was extracted with diethyl ether and the combined ether extract was washed with water, dried over Na2SO4 and evaporated under reduced pressure. The resulting oil was dissolved in diethyl ether and saturated with gaseous hydrochloric acid. The precipitated 2-(N,N-diethylaminomethyl)-4,5-methylenedioxyphenyl-n-butyrate.HCl (compound no. 62) was filtered off and recrystallized from methanol/diethyl ether; m.p. 126°–128° C.

In a similar manner the compounds having formula 1 wherein Z is methylene and R1–R5 have the meaning mentioned in table C were obtained.

EXAMPLE IV

5-N-(2-phenylethyl)aminomethyl-6-phenylmethoxy-1,3-benzodioxole.HCl

To a solution of 6-benzyloxy-3,4-methylenedioxybenzaldehyde (2.0 g, 7.8 mmol) in benzene (75 ml) were added phenethylamine (0.94 g, 7.8 mmol) and a catalytic amount of p-toluenesulphonic acid. The reaction mixture was heated at reflux temperature overnight using a Dean-Stark trap. The reaction mixture was cooled to room temperature and evaporated in vacuo. The residue was dissolved in dry THF, and lithiumaluminium hydride (0.6 g, 16 mmol) was added. The mixture was heated at reflux temperature for 20 hours under nitrogen and then cooled to room temperature. Excess LiAlH4 was decomposed by cautious addition of Na2SO4.10 H2O. The solid was filtered off and washed with two portions of hot tetrahydrofuran. The combined THF solution was evaporated under reduced pressure to give a yellow oil. The oil was dissolved in isopropanol/diethyl ether and saturated with gaseous hydrochloride. The precipitated 5-N-(2-phenylethyl)aminomethyl-6-phenylmethoxy-1,3-benzodioxole.HCl (compound no. 66) was filtered off and recrystallized from ethyl acetate; melting point 188°–190° C.

In a similar manner compounds of formula 1 wherein Z is methylene and R1–R5 have the meaning given in table D were obtained.

EXAMPLE V

5-N-[2-(3,4-dimethoxyphenyl)ethyl]-N-methyl-aminomethyl-6-phenylmethoxy-1,3-benzodioxole.

Sodium cyanoborohydride (0.34 g, 5.4 mmol) was added to a solution of 5-N-[2-(3,4-dimethoxyphenyl)ethyl]aminomethyl-6-phenylmethoxy-1,3-benzodioxole (1.42 g, 3.37 mmol) and aqueous formaldehyde (37% solution, 1.25 ml, 15.4 mmol) in acetonitrile (10 ml). The reaction mixture was stirred for 20 minutes at room temperature. The reaction mixture was made neutral by dropwise addition of glacial acetic acid. Stirring was continued for 5 hours. The solvent was removed under reduced pressure and the residue was partitioned between 2N potassium hydroxide solution (25 ml) and diethyl ether (25 ml). The aqueous layer was further extracted with two portions of diethyl ether and the combined organic extract was washed with 0.5N KOH solution and with water. The ether solution was extracted with 10% hydrogen chloride solution. The combined aqueous extract was made a alkaline with sodium hydroxide pellets and the solution was extracted with diethyl ether. The combined diethyl ether extract was washed with water, dried over Na2SO4 and evaporated under reduced pressure to give 1.03 g (yield 70%) of 5-N-[2-(3,4-dimethoxyphenyl)ethyl]-N-methyl-aminomethyl-6-phenylmethoxy-1,3-benzodioxole (compound no. 76); melting point 78°–80° C.

In a similar manner compounds having formula 1, wherein Z and R1–R5 have the meanings given in table E were obtained.

TABLE E

| No | R1 + R2 | R3 | R4 | R5 | Z | salt | m.p. (°C.) |
|---|---|---|---|---|---|---|---|
| 77 | —(CH2)— | CH3 | CH2C6H5 | n-C5H11 | CH2 | HCl | 169–170 |
| 78 | —(CH2)— | CH3 | (CH2)2C6H5 | n-C4H9 | CH2 | HCl | 99–102 |

We claim:

1. Compounds having anti-ischaemic activity of the formula

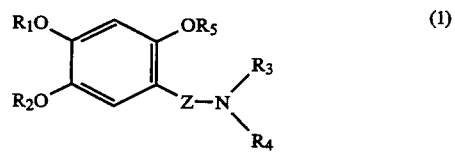

(1)

wherein:

$R_1+R_2$ together form an alkylene group having 1-3 C-atoms which may be substituted with one or more alkyl group(s) having 1-3 C-atoms;

Z is methylene optionally substituted with one or two alkyl group(s) having 1-3 C-atoms, or with one phenyl group or phenylalkyl group with 1-3 C-atoms in the alkyl group, which phenyl groups may be substituted with a group $(R_6)_p$ wherein $R_6$ is halogen, hydroxy, alkyl or hydroxyalkyl having 1-5C-atoms, alkoxy having 1-3 C-atoms, S-alkyl, S(O)-alkyl or S(O)$_2$-alkyl having 1-3 C-atoms, amino, mono- or dialkylamino having 1-3 C-atoms per alkyl group, trifluoromethyl, trifluoromethoxy, a sulphonylamido group SO$_2$NHR or a carbalkoxy group COOR wherein R is alkyl having 1-4 C-atoms, the group COOH, SO$_3$H, COHN$_2$, the amidino group or cyano group, and p has the value 0-3;

wherein $R_3+R_4$ together with the nitrogen atom form a saturated or unsaturated heterocyclic group of 5-7 ring atoms, which may contain a second hetero-atom from the group consisting of oxygen, sulphur and nitrogen, which ring may be substituted with a group $(R_6)_p$ wherein $R_6$ and p have the above mentioned meanings, or with phenylalkyl, phenylalkenyl, thienylalkenyl, pyridinylalkenyl, phenylalkynyl, thienylalkynyl or pyridinylalkynyl having at most 3 C-atoms in the alkyl, alkenyl or alkynyl part, which groups may be substituted with a group $(R_6)_p$ wherein $R_6$ and p have the above-mentioned meanings, or which ring may be fused with a phenyl group;

$R_5$ is alkyl having 1-12 C-atoms, alkenyl or alkynyl having 3-12 C-atoms, cycloalkyl having 3-8 C-atoms, cycloalkyl-alkyl having 3-8 ring atoms and 1-5 C-atoms in the alkyl group, phenylalkyl Or heteroaryl-alkyl having 1-5 C-atoms in the alkyl sub-group, phenylalkenyl, heteroaryl-alkenyl, phenylalkynyl or heteroaryl-alkynyl having 3-5 C-atoms in the alkenyl sub-group or alkynyl sub-group, which groups may be substituted with a group $(R_6)_p$, wherein $R_6$ and p have the above-mentioned meanings, and which alkyl sub-groups, alkenyl sub-groups and alkynyl sub-groups may contain a group —O—, —S— or CO, or a pharmacologically acceptable salt thereof.

2. Compositions having anti-ischaemic activity which comprise an anti-ischaemic effective amount of at least one compound as claimed in claim 1 as an active component.

3. A method of treating ischaemia, said method comprising administering an anti-ischaemic effective amount of a composition according to claim 2.

* * * * *